United States Patent [19]
Chang et al.

[11] Patent Number: 5,453,555
[45] Date of Patent: Sep. 26, 1995

[54] SELECTIVE 1,2-DIARYLETHANE SYNTHESIS

[75] Inventors: Clarence D. Chang, Princeton, N.J.; Stuart D. Hellring, Yardley, Pa.

[73] Assignee: Mobil Oil Corp., Fairfax, Va.

[21] Appl. No.: 158,172

[22] Filed: Nov. 22, 1993

Related U.S. Application Data

[63] Continuation of Ser. No. 963,977, Oct. 21, 1992, abandoned.
[51] Int. Cl.$^6$ .................................. C07C 1/20; C07C 2/66
[52] U.S. Cl. .......................... 585/469; 585/446; 585/467
[58] Field of Search ....................... 585/446, 467, 585/469, 425, 24, 25, 27

[56] References Cited

U.S. PATENT DOCUMENTS

| | | | |
|---|---|---|---|
| 4,112,008 | 9/1978 | Mancilly | 585/458 |
| 4,469,908 | 9/1984 | Burress | 585/467 |
| 4,665,256 | 5/1987 | Diaris et al. | 585/467 |
| 4,751,340 | 6/1988 | Pellet | 585/467 |
| 4,962,256 | 10/1990 | Le et al. | 585/467 |
| 5,001,283 | 3/1991 | Altman et al. | 568/867 |

*Primary Examiner*—P. Achutamurthy
*Attorney, Agent, or Firm*—Alexander J. McKillop; Dennis P. Santini; Edward F. Kenehan, Jr.

[57] ABSTRACT

There is provided a process for reacting a 2-arylethanol, such as 2-phenethanol, with an aromatic compound, such as toluene, to produce a 1,2-diarylethane, such as 2-phenethyltoluene. The reaction involves the use of a catalyst comprising an acidic solid oxide, such as ZSM-5, zeolite Beta, MCM-22 or ZSM-12.

2 Claims, No Drawings

SELECTIVE 1,2-DIARYLETHANE SYNTHESIS

CROSS-REFERENCE TO RELATED APPLICATION

This application is continuation of U.S. application Ser. No. 07/963,977, filed Oct. 21, 1992, now abandoned.

BACKGROUND

There is provided a process for reacting a 2-arylethanol with an aromatic compound over an acidic solid oxide catalyst to produce a 1,2-diarylethane.

Diarylalkanes are commercial commodity and fine chemicals. They may be hydrogenated for use as traction fluids, oils for cosmetics (BASF DE507175), or pharmaceuticals. Diarylethanes are used as industrial solvents for applications such as carbonless copypaper.

SUMMARY

There is provided a process for preparing a 1,2-diarylethane, said process comprising reacting a 2-arylethanol with an aromatic compound over catalyst comprising an acidic solid oxide under conditions sufficient to produce said 1,2-diarylethane.

DESCRIPTION 1,2-Diarylethanes are produced selectively over the competing 1,1-diarylethane isomers by aromatic alkylation with 2-arylethanols over acidic solid oxide catalysts. In contrast, aromatic alkylation with styrene gives the branched 1,1-diarylethanes as the major isomers. These differences in isomer product distribution indicate that alkylation with 2-arylethanols does not proceed appreciably through dehydration to styrene or through an intermediate similar to that involved with styrene. Medium-pore zeolites such as ZSM-5, as well as large-pore zeolites such as zeolite Beta, ZSM-12, MCM-22 may serve as catalysts for this reaction. Activity, catalyst aging, and selectivity of the aromatic substitution are affected by the choice of zeolite.

The catalyst used in the present process comprises at least one acidic solid oxide. Examples of such acidic solid oxides include aluminosilicates and materials, such as SAPO's, which contain oxides of elements other than silicon and aluminum. These acidic solid oxides may be amorphous or crystalline materials. The crystalline materials may have non-layered, 3-dimensional framework structures, or layered structures, such as the layered structures of clays. Preferred acidic solid oxides are zeolites, particularly medium-pore size and large-pore size zeolites.

A convenient measure of the extent to which a zeolite provides control of access to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g., less than 5 Angstroms. On the other hand, zeolites which provide relatively free access to the internal zeolite structure have a low value for the Constraint Index, and usually pores of large size, e.g., greater than 8 Angstroms. The method by which Constraint Index is determined is described fully in U.S. Pat. No. 4,016,218, incorporated herein by reference for details of the method.

A zeolite which may be used in the present reaction may be a medium- or large-pore size zeolite. This zeolite may have a Constraint Index of 12 or less. Zeolites having a Constraint Index of 2-12 are generally regarded to be medium-pore size zeolites. Zeolites having a Constraint Index of less than 1 are generally regarded to be large-pore size zeolites. Zeolites having a Constraint Index of 1-2 may be regarded as either medium- or large-pore size zeolites.

The members of the class of medium-pore size zeolites may have an effective pore size of generally from about 5 to about 8 Angstroms, such as to freely sorb normal hexane. In addition, the structures provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the medium-pore size type. Windows of 10-membered rings are preferred, although, in some instances, excessive puckering of the rings or pore blockage may render these zeolites ineffective.

Although 12-membered rings in theory would not offer sufficient constraint to constitute a medium-size pore, it is noted that the puckered 12-ring structure of TMA offretite does show some constrained access. Other 12-ring structures may exist which may be regarded to be medium-pore sized, and therefore, it is not the present intention to classify a particular zeolite solely from theoretical structural considerations.

| | CI (at test temperature) | |
|---|---|---|
| ZSM-4 | 0.5 | (316° C.) |
| ZSM-5 | 6–8.3 | (371° C.–316° C.) |
| ZSM-11 | 5–8.7 | (371° C.–316° C.) |
| ZSM-12 | 2.3 | (316° C.) |
| ZSM-20 | 0.5 | (371° C.) |
| ZSM-22 | 7.3 | (427° C.) |
| ZSM-23 | 9.1 | (427° C.) |
| ZSM-34 | 50 | (371° C.) |
| ZSM-35 | 4.5 | (454° C.) |
| ZSM-38 | 2 | (510° C.) |
| ZSM-48 | 3.5 | (538° C.) |
| ZSM-50 | 2.1 | (427° C.) |
| TMA Offretite | 3.7 | (316° C.) |
| TEA Mordenite | 0.4 | (316° C.) |
| Mordenite | 0.5 | (316° C.) |
| Clinoptilolite | 3.4 | (510° C.) |
| Mordenite | 0.5 | (316° C.) |
| REY | 0.4 | (316° C.) |
| Amorphous Silica-alumina | 0.6 | (538° C.) |
| Dealuminized Y (Deal Y) | 0.5 | (510° C.) |
| Erionite | 38 | (316° C.) |
| Zeolite Beta | 0.6–2.0 | (316° C.–399° C.) |

The above-described Constraint Index provides a definition of those zeolites which are particularly useful in the present process. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g., temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood to those skilled in the art that the CI, as utilized herein, while affording a highly useful means for characterizing the zeolites of interest is approximate, taking into consideration the manner of its determination, with the possibility, in some instances, of compounding variable extremes. However, in all instances, at a temperature within the above-specified range of 290° C. to about 538° C., the CI will have a value for any given zeolite of particular interest herein of 12 or less.

Examples of zeolites having a Constraint Index of from 1 to 12 include ZSM-5, ZSM-11, ZSM-12, ZSM-22, ZSM-23, ZSM-35, ZSM-38, and ZSM-48.

ZSM-5 is described in greater detail in U.S. Pat. Nos. 3,702,886 and Re. 29,948. The entire descriptions contained within those patents, particularly the X-ray diffraction pattern of therein disclosed ZSM-5, are incorporated herein by reference.

ZSM-11 is described in greater detail in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-22 is described in U.S. Pat. No. 4,556,477, the entire contents of which is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,406,859. The description of that zeolite, and particularly the specified X-ray diffraction pattern thereof, is incorporated herein by reference.

ZSM-48 is more particularly described in U.S. Pat. No. 4,234,231, the entire contents of which is incorporated herein by reference.

The large-pore zeolites, including those zeolites having a Constraint Index less than 2, are well known to the art and have a pore size sufficiently large to admit the vast majority of components normally found in a feed chargestock. The zeolites are generally stated to have a pore size in excess of 7 Angstroms and are represented by zeolites having the structure of, e.g., Zeolite Beta, Zeolite Y, Ultrastable Y (USY), Dealuminized Y (Deal Y), Mordenite, ZSM-3, ZSM-4, ZSM-18, and ZSM-20. A crystalline silicate zeolite well known in the art and useful in the present invention is faujasite. The ZSM-20 zeolite resembles faujasite in certain aspects of structure, but has a notably higher silica/alumina ratio than faujasite, as does Deal Y.

Although zeolite Beta has a Constraint Index less than 2, it is to be noted that it does not have the same structure as the other large-pore zeolites, nor does it behave exactly like a large-pore zeolite. However, zeolite Beta is a particularly preferred zeolite for use in the present reaction.

Zeolite ZSM-4 is described in U.S. Pat. No. 3,923,639, to which reference is made for details of this catalyst.

Zeolite ZSM-20 is described in U.S. Pat. No. 3,972,983, to which reference is made for details of this catalyst.

Zeolite Beta is described in U.S. Pat. Nos. 3,308,069, and Re. No. 28,341, to which reference is made for details of this catalyst.

Low sodium Ultrastable Y molecular sieve (USY) is described in U.S. Pat. Nos. 3,293,192 and 3,449,070, to which reference is made for details of this catalyst.

Dealuminized Y zeolite (Deal Y) may be prepared by the method found in U.S. Pat. No. 3,442,795, to which reference is made for details of this catalyst.

Zeolite UHP-Y is described in U.S. Pat. No. 4,401,556, to which reference is made for details of this catalyst.

Another zeolite which may be used in the present reaction is MCM-22. MCM-22 is described in U.S. Pat. No. 4,954,325, as well as in U.S. Pat. No. 5,107,054, the entire disclosures of which are expressly incorporated herein by reference.

The zeolite crystals can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

It may be desired to incorporate the zeolite with another material which is resistant to the temperatures and other conditions employed in the present process. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. Inactive materials suitably serve as diluents to control the amount of conversion so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commerical use, it is desirable to prevent the catalyst from breaking down into powder-like materials. These clay binders have been employed normally only for the purpose of improving the crush strength of the catalyst.

Naturally occurring clays which can be composited with zeolite crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

In addition to the foregoing materials, the crystals can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia. It may also be advantageous to provide at least a part of the foregoing matrix materials in colloidal form so as to facilitate extrusion of the bound catalyst component(s).

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

In the reaction zone, the reaction temperature may be at least 25° C., e.g., from 25° C. to 450° C., e.g., from 200° C. to 300° C. Pressures range from 25 up to 5000 psig. The preferred range is from 200 to 400 psig. Liquid hourly space velocity may be from 0.1 to 5 $hr^{-1}$, more usually 0.5 to 2.

The amounts of 2-arylethanol and aromatic compound in the reaction zone may be sufficient amounts, e.g., amounts which are sufficient to produce the desired amount of product.

Examples of 2-arylethanol reactants include 2-phenyl, 2-tolyl, 2-xylyl, 2-ethylbenzyl, and 2-naphthyl ethanol. The aryl rings of the 2-arylethanols may be unsubstituted or substituted, e.g., with alkyl or aryl groups. In addition the ethanol portion of the 2-arylethanols may be substituted as in

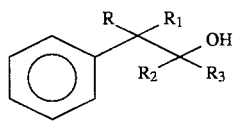

where R, $R_1$, $R_2$, $R_3$ may be alkyl, aryl, or H.

Examples of aromatic compound reactants include benzene, toluene, xylenes, mesitylenes, durenes, naphthalenes, and other alkyl or aryl substituted aromatic ring compounds.

EXAMPLES

Feeds were prepared by dissolving either styrene or 2-phenethanol in toluene. A stainless steel fixed-bed reactor (0.25 in. O.D.×0.35 in. wall) was used with 3 ml zeolite zoned by vycor. Hydrocarbons were analyzed by GC using a DB-1 capillary column. Regioisomers were separated using an 80/120 carbopak B/3% SP-1500 stainless steel packed column. Regioisomers were identified from authentic samples where available. Ortho-, meta-, and para-2-phenethyltoluenes were prepared separately by reaction of benzene with the corresponding 2-, 3-, or 4-methylphenethanols (Aldrich), isolated and examined by NMR. The GC retention times of these derivatives were used to identify isomers in the toluene/2-phenethanol reactions.

ZSM-12 was used as an alumina extrudate (65% zeolite, $SiO_2/Al_2O_3=250$). Zeolite Beta and ZSM-5 were used as pure zeolite.

Data comparing product distributions for styrene and 2-phenethanol over ZSM-12 under identical operating conditions are shown in Table 1. Data comparing 2-phenethanol over ZSM-12, zeolite Beta, and ZSM-5 under identical conditions are shown in Table 2.

TABLE 1

Comparison Between Toluene Phenethylation by Either Styrene or 2-Phenethanol
Conditions: 10 mol % 2-Phenethanol or Styrene in Toluene, 250° C., 300 psig, 1 LHSV

| Catalyst | ZSM-12 | ZSM-12 |
|---|---|---|
| Product Distribution (wt %) | | |
| 2-Phenethyltoluenes | 0.2 | 10.1 |
| 1-Phenethyltoluenes | 4.4 | 2.0 |
| Benzene | 1.4 | 0.1 |
| Toluene | 86.3 | 81.4 |
| Ethylbenzene | 0.1 | 0.1 |
| 2-Phenethanol | — | 0.0 |
| Toluene dimer | 0.1 | 0.0 |
| Styrene dimer | 5.4 | 0.3 |
| Others | 1.3 | 0.3 |
| Water | — | 1.9 |
| Polymer | 0.8 | 3.8 |
| Selectivity Based on Toluene (mol %) | | |
| Phenethyltoluenes | 95.2 | 99.6 |
| Toluene dimer | 4.8 | 0.3 |
| Selectivity Based on (mol %): | Styrene | 2-Phenethanol |
| Phenethyltoluenes | 22.9 | 59.2 |
| Benzene | 17.4 | 1.6 |
| Ethylbenzene | 1.2 | 1.5 |
| Styrene dimer | 51.0 | 2.5 |
| Polymer | 7.5 | 35.1 |
| Toluene Conversion | 2.7 | 6.5 |
| Styrene Conversion | 100.0 | — |
| 2-Phenethanol Conversion | — | 99.9 |
| 2-/ 1-Phenethyltoluene Ratio | 0.0 | 5.1 |

TABLE 2

Reaction of 2-Phenethanol and Toluene over Zeolites
Conditions: 25 mol % 2-Phenethanol in Toluene, 250° C., 300 psig, 1 LHSV

| Catalyst | ZSM-12 | Zeolite Beta | ZSM-5 |
|---|---|---|---|
| Product Distribution (wt %) | | | |
| 2-Phenethyltoluenes | 16.7 | 4.6 | 10.8 |
| 1-Phenethyltoluenes | 4.0 | 0.7 | 5.6 |
| Benzene | 0.4 | 0.7 | 0.9 |
| Toluene | 59.0 | 66.2 | 61.2 |
| Ethylbenzene | 0.8 | 1.1 | 0.7 |
| 2-Phenethanol | 0.1 | 1.2 | 0.2 |
| Toluene dimer | 0.3 | 0.4 | 0.2 |
| Styrene dimer | 0.4 | 0.1 | 3.0 |
| Diphenethylether | 0.0 | 2.9 | 0.0 |
| Others | 1.5 | 1.0 | 11.2 |
| Water | 4.6 | 4.6 | 4.6 |
| Polymer | 12.4 | 16.7 | 11.5 |
| Selectivity Based on Toluene (mol %) | | | |
| Phenethyltoluenes | 97.3 | 85.9 | 97.9 |
| Toluene dimer | 2.8 | 14.1 | 2.1 |
| Selectivity Based on 2-Phenethanol (mol %) | | | |
| Phenethyltoluenes | 43.7 | 11.5 | 34.8 |
| Benzene | 2.2 | 3.7 | 4.8 |
| Ethylbenzene | 3.0 | 4.6 | 2.6 |

TABLE 2-continued

Reaction of 2-Phenethanol and Toluene over Zeolites
Conditions: 25 mol % 2-Phenethanol in Toluene,
250° C., 300 psig, 1 LHSV

| Catalyst | ZSM-12 | Zeolite Beta | ZSM-5 |
|---|---|---|---|
| Styrene dimer | 1.4 | 0.5 | 11.9 |
| Diphenethylether | 0.0 | 10.9 | 0.0 |
| Polymer | 49.6 | 68.9 | 45.9 |
| Normalized 2-Phenethyltoluenes | | | |
| ortho | 60.6 | 45.0 | 35.0 |
| meta | 21.7 | 27.8 | 35.4 |
| para | 17.7 | 27.2 | 29.6 |
| Toluene Conversion | 14.5 | 4.1 | 11.4 |
| 2-Phenethanol Conversion | 99.8 | 96.3 | 97.5 |
| 2-/ 1-Phenethyltoluene Ratio | 4.2 | 6.6 | 1.9 |

Data in Table 1 show that styrene yields mostly styrene dimer (51.0%), phenethyltoluenes (22.9%), and benzene (17.4%). Of the phenethyltoluenes formed, the ratio of 1-phenethyltoluene/ 2-phenethyltoluene was about 22. With 2-phenethanol, however, the major products were phenethyltoluenes (59.2%) and polymer (35.1%). Of the phenethyltoluenes formed, the ratio of 2-phenethyltoluene/ 1-phenethyltoluene was about 5.1. This indicates that 2-phenethanol does not dehydrate to styrene under these reaction conditions, and that the dehydration intermediate (presumably a phenonium ion) is more susceptible to polymerization over these zeolites. Note also that the aromatic alkylation activity of 2-phenethanol appears greater than that of styrene.

Data in Table 2 show activity and selectivity vary with zeolite structure. Zeolite Beta, which is the largest pore material studied, showed lower activity and lower selectivity than did smaller pore material ZSM-12 and ZSM-5. These may be related in that zeolite Beta seemed to rapidly age under these conditions, and the reactor eventually plugged with polymer. Apparently polymerization on the catalyst under fixed-bed conditions causes catalyst aging and suggests a stirred tank reactor might be preferred for this process. ZSM-12 had slightly higher activity and selectivity for phenethyltoluene formation than did ZSM-5. This seems consistent with the large shape of these products.

Interestingly, the different zeolites gave some variation in regioselectivity in the position of alkylation on toluene. The larger pore ZSM-12 gave mostly ortho-isomer which is consistent with toluene being an ortho-, para-director with twice as many ortho as para positions. Apparently, some isomerization to meta product also occurs under these conditions. Medium-pore ZSM-5 gave about equal amounts of all three isomers, which is consistent with its para-selective nature in such reactions to form the most linear product. The selectivity of zeolite Beta must be interpreted more carefully since its pore dimensions are likely to be significantly altered by extensive collection of polymer on the catalyst.

Dehydration of 2-phenethanol to styrene over zeolites is disclosed (Nippon Sheet Glass KK JP-194492, 1984) under conditions similar to those employed in the above Examples. Styrene dimerization over zeolites is well known and gives products consistent with an intermediate benzylic carbocation. Cracking of diarylethanes to styrene derivatives also is disclosed (Innes, R. A. and M. L. Occelli, *J. Molecular Catal.*, 32, 259 (1985)). This cracking represents the reverse reaction of the aromatic alkylation relevant to the current concept. From these disclosures one might conclude that 2-phenethanol would form styrene under aromatic alkylation conditions and would yield 1,1-diarylethane products identical to styrene.

Typically, aromatic alkylation with olefins or alkylhalides under Friedel-Crafts conditions gives similar products which result from equilibration of carbocation intermediates. Aromatic substitution with 2-phenethylhalides under Friedel-Crafts conditions is known to give 1,2-diarylethane products with high selectivity. If this followed a simple carbocation equilibration mechanism, the expected product would result from a benzylic species similar to that from styrene. Both would be expected to give the same product distribution. The difference has been explained by anchimeric assistance from the phenyl ring to give an intermediate phenonium ion. Spectroscopic evidence indicates that the formation of the phenonium ion intermediate is a parallel path with benzylic carbocation formation and that the two do not interconvert-directly. The present data indicate that anchimeric assistance can be captured over zeolite catalysts in competition with dehydration to styrene. 1,2-disubstituted ethanes are formed from 2-phenethanol in higher selectivity than the 1,1-disubstituted ethanes. Styrene produces the opposite.

What is claimed is:

1. A process for preparing a mixture of ortho, meta and para isomers of 2-phenethyltoluene, said process comprising reacting 2-phenethanol with toluene over a catalyst comprising an acidic solid oxide under conditions sufficient to produce said isomers of 2-phenethyltoluene, wherein said acidic solid oxide is a zeolite selected from the group consisting of ZSM-5, ZSM-12, MCM-22 and zeolite Beta, and wherein the reaction conditions include a temperature of from 25° C. to 450° C., a pressure of from 25 psig to 5000 psig and a liquid hourly space velocity of from 0.1 hr$^{-1}$ to 5 hr$^{-1}$.

2. A process according to claim 1, wherein said zeolite is ZSM-12.

* * * * *